US00PP26534P3

(12) United States Plant Patent
Olesen

(10) Patent No.: US PP26,534 P3
(45) Date of Patent: Mar. 29, 2016

(54) MINIATURE ROSE PLANT NAMED 'POULTY017'

(50) Latin Name: ***Rosa* hybrid**
Varietal Denomination: Poulty017

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 236 days.

(21) Appl. No.: 13/986,910

(22) Filed: Jun. 14, 2013

(65) Prior Publication Data

US 2014/0373215 P1 Dec. 18, 2014

(51) Int. Cl.
*A01H 5/00* (2006.01)
*A01H 5/02* (2006.01)

(52) U.S. Cl.
USPC ..... Plt./121
CPC ..... *A01H 5/0222* (2013.01)

(58) Field of Classification Search
USPC ..... Plt./121
See application file for complete search history.

(56) References Cited

PUBLICATIONS

Perfection by Poulsen Indoor Roses Main varieties 2013. Jan. 2013.*

* cited by examiner

*Primary Examiner* — Annette Para

(57) ABSTRACT

A new miniature rose plant that has abundant, deep pink flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulty017'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulty017', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant deep pink flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulty017' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulty017' was selected by the inventor as a single plant from the progeny of the hybridization in 2007.

Asexual reproduction of 'Poulty017' by cuttings was first done by Mogens N. Olesen in the nursery in Fredensborg, Denmark in 2008. This initial and other subsequent propagations conducted in controlled environments have demonstrated that the characteristics of 'Poulty017' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty017'.

Specifically illustrated in the drawing are flowers at various stages of development, flower in parts, leaves, and stems.

DETAILED DESCRIPTION OF THE VARIETY

The following is a description of 'Poulty017', as observed in its growth in glasshouses in Burlington, Ontario, Canada. Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poultin', U.S. Plant Pat. No. 10,164 are compared to 'Poulty017' in Chart 1.

CHART 1

| | 'Poulty017' | 'Poultin' |
|---|---|---|
| Petalage: | 60 petals total, 8 of which are petaloids | 20-25 |
| Flower Diameter: | 35 mm | 1.75-2 inches (44-50 mm) |
| Flower petal upper surface color: | Red Group 53C | Red Purple Group 58B |

Flower and Flower Bud

Blooming habit: Continuous.

Flower bud:

*Size.*—Upon opening, 20 mm in length from base of receptacle to end of bud. 11 mm in diameter.

*Bud form.*—Urceolate.

*Bud color.*—As sepals unfold, petals are Red Group 53C.

*Sepals.*—Upper Surface: Color: Green Group 138A. Texture: Smooth, weak pubescence. Lower Surface: Color: Yellow Green Group 144A. Texture: Smooth. Shape: Apex: Cirrhose. Base: Flat at union with receptacle. Margins: Margins have weak foliaceous appendages on three of the five sepals. Size: 28 mm long by 5 mm wide.

*Receptacle.*—Surface Texture: Smooth. Shape: Campanulate. Size: 5 mm tall and Y mm wide. Color: Yellow Green Group 144A.

*Pedicel.*—Surface: Smooth. Length: 15 to 25 mm. Diameter: Generally 2 mm. Color: Yellow-Green Group 144A. Strength: Strong.

*Borne.*—Singly.

Flower bloom:

*Fragrance.*—Light floral spicy scent.

*Duration.*—As a pot plant, flowers last up to 28 days.

*Size.*—Flower diameter is 35 mm when open. Flower depth is 20 mm.

*Form.*—General shape is a hybrid tea with a high pointed, tightly closed, center.

*Shape of flower, side view.*—Upon opening, the upper portion is flat. The lower portion is a flattened convex.

Petalage: Under normal conditions, flowers have 60 petals total, 8 of which are petaloids.

Color:

*General tonality.*—On open flower Red Group 53C with intonations of Red-Purple Group 58B.

Petals:

*Petal color.*—Upon opening upper surface is Red Group 53C, with a petal spot of Yellow Group 4C. Lower surface Red Purple Group 63A with a petal spot of Yellow Group 4C. After opening, the coloration described above remains.

*Petal reflex.*—Weak.

*Margin.*—Entire, with a slight point at the center. No undulations of margin.

*Shape.*—Generally broad and elliptic. Apex shape: Rounded. Base shape: Acute.

*Size.*—21 mm (l) by 21 mm (w).

*Texture.*—Smooth.

*Thickness.*—Average.

Petaloids:

*Quantity.*—8 on average.

*Shape.*—Irregular, and asymmetric. The apex and base are acute.

*Color.*—Upper surface is Red Group 53C, with a petal spot of Yellow Group 4C. Lower surface is Red Purple Group 63A with a petal spot of Yellow Group 4C.

*Size.*—6 mm (l) by 5 mm (w).

Reproductive organs:

*Pollen.*—None Observed.

*Anthers.*—Size: 1 mm long. Color: Yellow Group 13B. Quantity: 20 on average.

*Filaments.*—Color: Yellow Group 1D. Length: About 3 mm.

*Pistils.*—Length: About 2 mm long. Quantity: 15 on average.

*Stigmas.*—Slightly inferior relative to the length of the filaments and the height of the anthers. Color: Green White Group 157A.

*Styles.*—Color: Green White Group 157A.

*Seed formation.*—Not observed.

Plant

Plant growth: Upright. Plants are 16 cm in height, and 13 cm wide.

Stems:

*Color.*—Juvenile growth: Yellow-Green Group 144A. Mature growth: Yellow-Green Group 146A.

*Length.*—Canes are 12 cm from the base of the plant to the flowering portion.

*Diameter.*—3 mm.

*Internodes.*—On mature canes, there is an average distance of 25 mm between nodes.

*Surface texture.*—Young and mature wood is smooth.

Prickles: None observed.

Plant foliage:

*Compound leaf size.*—75 mm (l) by 42 mm (w).

*Quantity.*—3 leaves per 10 cm of stem.

*Color of juvenile foliage.*—Upper Leaf Surface: Yellow-Green Group 146B. Lower Leaf Surface: Yellow-Green Group 146C. Margins: Greyed-Red Group 180A.

*Color of mature foliage.*—Upper Leaf Surface: Yellow-Green Group 147A. Lower Leaf Surface: Yellow-Green Group 148B.

Plant leaves and leaflets:

*Stipules.*—Size: About 5 mm in length. Shape: Linear, slightly broad based with outward extending apecies. Margins: Finely serrated with few stipitate glands. Color: Yellow-Green Group 146A.

*Petiole.*—Length: 20 mm on average. Diameter: About 1 mm. Upper surface: Yellow-Green Group 144A. Lower surface: Yellow-Green Group 144B.

*Rachis.*—Length: 25 mm on average. Diameter: About 2 mm. Upper surface: Yellow-Green Group 144A. Lower surface: Yellow-Green Group 144B.

*Leaflet.*—Number of leaflets: 5 on normal leaves in middle of the stem. Size: 30 mm in length by 18 mm wide. Margin: Serrate. General Shape: Elliptical. Apex Shape: Acute. Base Shape: Round. Texture: Smooth. Arrangement: Odd pinnate. Venation: Reticulate. Leaf Gloss: Somewhat glossy.

Cold hardiness: The variety is tolerant to USDA Cold Hardiness Zone 6.

Heat tolerance: The variety has been found to be suitable for climate conditions found in the American Horticulture Society heat zone 7.

It is claimed:

1. A new and distinct variety of rose plant of the miniature class named 'Poulty017', substantially as illustrated and described herein, due to its abundant, deep pink flowers, vigorous growth, compact habit, suitability for production from softwood cuttings in pots, and durable flowers and foliage that make the variety suitable for distribution in the floral industry.

* * * * *

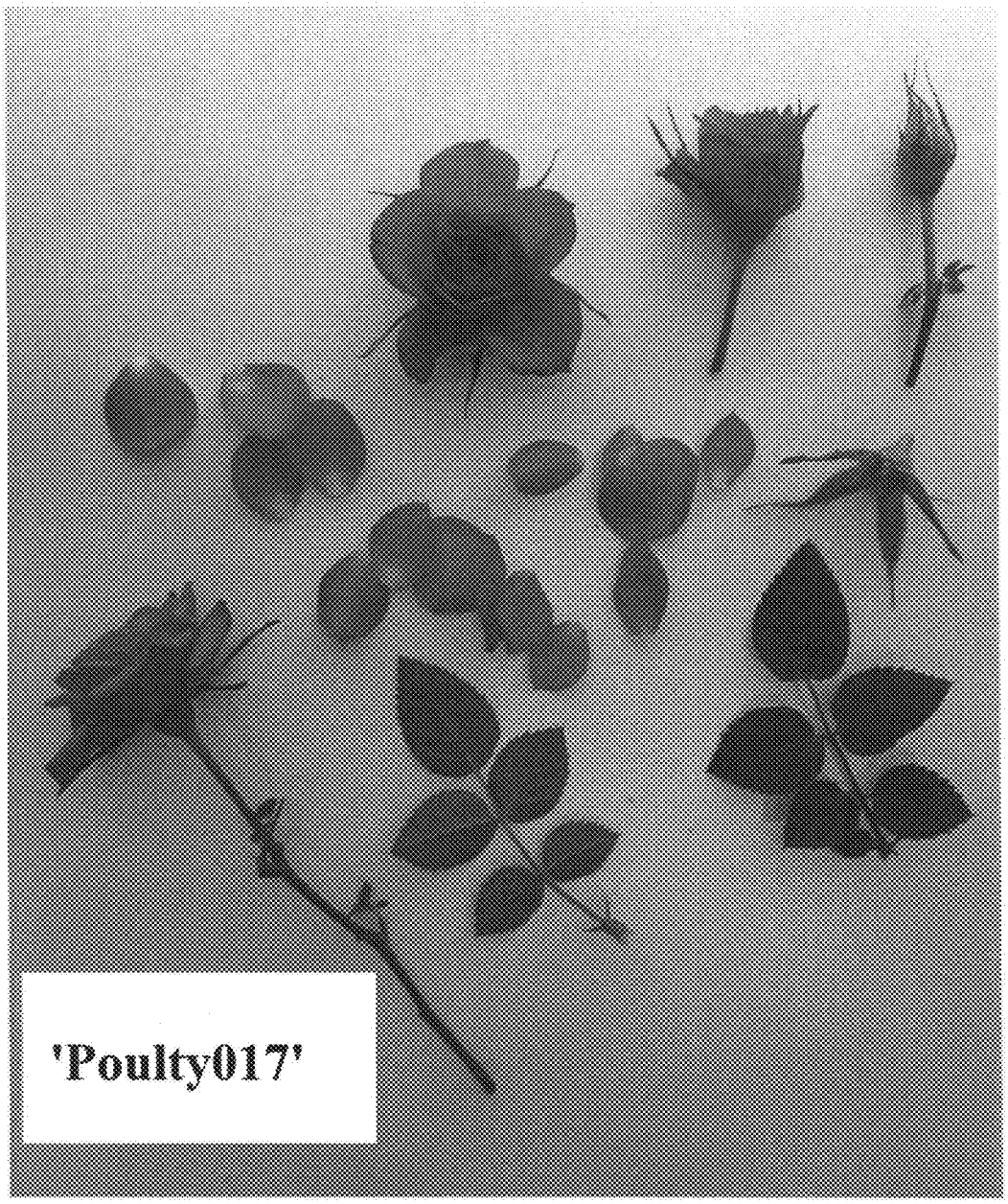
'Poulty017'